United States Patent
Kim et al.

(10) Patent No.: US 8,530,047 B2
(45) Date of Patent: *Sep. 10, 2013

(54) METHOD FOR POLYMERIZING A SMALL OLIGONUCLEOTIDE, AND USE OF A HIGH-MOLECULAR OLIGONUCLEOTIDE PREPARED BY THE POLYMERIZATION METHOD

(75) Inventors: KwangMeyung Kim, Seoul (KR); Ick Chan Kwon, Seoul (KR); Kui Won Choi, Seoul (KR); Seung Young Lee, Gyeonggi-Do (KR); In Chan Youn, Seoul (KR); Myung Sook Huh, Seoul (KR); So Jin Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/142,876

(22) PCT Filed: Mar. 2, 2010

(86) PCT No.: PCT/KR2010/001296
§ 371 (c)(1),
(2), (4) Date: Jun. 30, 2011

(87) PCT Pub. No.: WO2010/131835
PCT Pub. Date: Nov. 18, 2010

(65) Prior Publication Data
US 2011/0274930 A1    Nov. 10, 2011

(30) Foreign Application Priority Data
May 14, 2009  (KR) .................. 10-2009-0042273

(51) Int. Cl.
*B32B 5/16*    (2006.01)

(52) U.S. Cl.
USPC .......... 428/402; 428/403; 428/407; 514/44 R; 977/702

(58) Field of Classification Search
USPC ........ 428/402, 403, 407; 514/44 R; 977/702
See application file for complete search history.

(56) References Cited

U.S. PATENT DOCUMENTS

2010/0130588 A1 * 5/2010 Yaworski et al. ........... 514/44 A
2011/0223318 A1 * 9/2011 Choi et al. ................... 427/58

FOREIGN PATENT DOCUMENTS

KR    10-0466254    8/2003

OTHER PUBLICATIONS

Huh, MS, et al J.controlled release, vol. 144, pp. 134-143 (2010).*
Korean Office Action dated Dec. 29, 2011 issued in corresponding Korean Patent Application No. 10-2009-0042273.

* cited by examiner

*Primary Examiner* — Leszek Kiliman
(74) *Attorney, Agent, or Firm* — Staas & Halsey LLP

(57) ABSTRACT

The oligonucleotide polymerization method of the present invention is advantageous in that an oligonucleotide with a small molecular weight can be easily polymerized into high-molecular weight oligonucleotides. Further, the high-molecular oligonucleotide prepared by the method of the present invention can bind to hydrophilic high-molecular materials or inorganic materials, and then can be stably delivered to a living body. Therefore, the high-molecular oligonucleotide prepared by the method of the present invention can be widely used for treating various diseases.

12 Claims, 4 Drawing Sheets

METHOD FOR POLYMERIZING A SMALL OLIGONUCLEOTIDE, AND USE OF A HIGH-MOLECULAR OLIGONUCLEOTIDE PREPARED BY THE POLYMERIZATION METHOD

CROSS REFERENCE TO RELATED APPLICATIONS

This application is a national phase application, under 35 U.S.C. 371, of international application No. PCT/KR2010/001296, filed on Mar. 2, 2010, which claimed priority to Korean Patent Application No. 10-2009-0042273, filed on May 14, 2009, the disclosures of which are incorporated herein by reference.

TECHNICAL FIELD

The present invention relates to a method for preparing a high-molecular weight oligonucleotides having an increased in vivo stability by polymerizing an oligonucleotide with a small molecular weight, and the use of a high-molecular weight oligonucleotides prepared by the polymerization method.

BACKGROUND ART siRNA is a material which has come into the spotlight as a gene therapy since it was discovered as exhibiting an excellent effect in view of inhibiting expression of a specific gene in an animal cell. Such siRNA has been studied for the last 20 years by virtue of high activity and precise gene selectivity, and is expected as a drug, which may replace an antisense oligonucleotide (ODN) currently tried as a drug (medicine, therapy). Accordingly, more than 30 pharmaceutical companies and biotechnology companies are currently focused to develop on drug Based on the siRNA oligonucleotides (siRNA). Especially, they are developing oligonucleotide (siRNA) related therapies for treating several diseases, such as diabetes, obesity, rheumatism, Parkinson's disease, hepatitis B, hepatitis C, ADIS and cancers.

A drug which employs the conception of the oligonucleotide such as siRNA specifically break a certain specific mRNA in order to regulate an expression and metabolic process of a specific gene to suppress a transcription and protein synthesis of a target gene, thereby treating a disease. However, due to siRNA's low in vivo stability and susceptible to nuclease attack, it is easily degraded by various serum nucleases within body. Especially, for a therapy given through injection, the oligonucleotide may be degraded more fast unless chemically stably processed. Also, the oligonucleotide such as siRNA is difficult to penetrate a cell membrane having the same negative charge due to its anionic property. Consequently, the oligonucleotide may not be easily transferred into the cell, thereby causing a drastic reduction of therapy efficiency. Furthermore, the oligonucleotide such as siRNA may be identified as an external material in the living body, which may cause a side effect in an immune system. The oligonucleotide may also affect a gene present at another portion other than an originally expected gene portion, thereby causing cross-hybridization in a gene sequence.

Therefore, in order to ensure stability and minimize the side effect of the oligonucleotide (siRNA)-based drug used for disease treatment, it is required to develop drug carrier systems, such as polymeric-nanoparticles, micelles, and liposomes, which are capable of improving in vivo stability of a drug and minimize a side effect of the drug.

DISCLOSURE OF THE INVENTION

Therefore, to address the above-identified drawbacks, an aspect of this specification is to provide a high molecular weight oligonucleotides, which can be used for improving in vivo stability of an oligonucleotide such as siRNA and minimizing a side effect of a drug.

To achieve this and other advantages and in accordance with the purpose of the present invention, as embodied and broadly described herein, there is provided a high molecular oligonucleotide, which is prepared by polymerizing oligonucleotides with small molecular weights.

Also, to achieve the aspect of this specification, there is provided a high molecular weight oligonucleotides carrier system having stability more increased by binding the prepared high-molecular weight oligonucleotides to hydrophilic high-molecular materials or inorganic materials.

ADVANTAGEOUS EFFECT

The high-molecular oligonucleotide prepared by this specification can have an increased stability, as compared to an oligonucleotide with a small molecular weight, which has been conventionally used, resulting in an extension of a retention time in a living body and a stable suppression of expression of a target disease gene. Therefore, the high-molecular weight oligonucleotides can be effectively used for treating various diseases.

MODES FOR CARRYING OUT THE PREFERRED EMBODIMENTS

Figure 1:
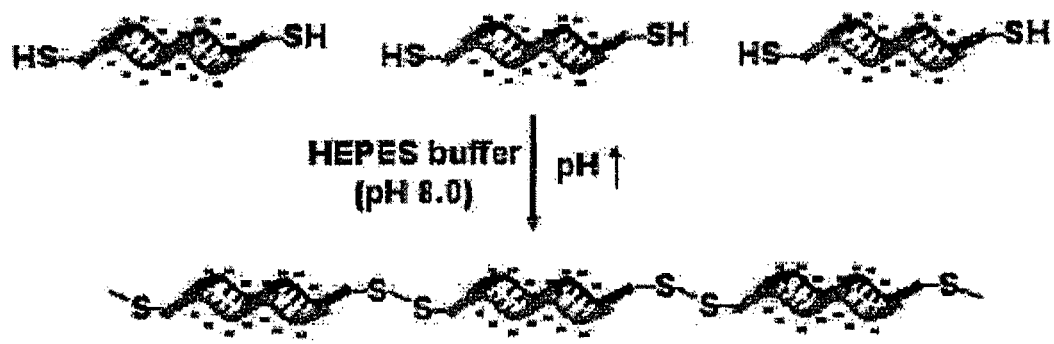
FIG. 1 is a mimetic diagram showing a preparation of an oligonucleotide (siRNA) with a high molecular weight using a disulfide bond of oligonucleotides (siRNA) having -thiol group (—SH group) at both terminals.

The present disclosure is characterized by providing a high-molecular oligonucleotide prepared by polymerizing oligonucleotides with small molecular weights.

Also, the present disclosure is characterized by providing a nanoparticle type carrier system, prepared by binding the high-molecular oligonucleotide prepared by the polymerization to hydrophilic high-molecular materials or inorganic materials.

Hereinafter, description will be given in detail of this specification.

Explaining this specification, "low-molecular oligonucleotide" or "oligonucleotide with a small molecular weight" indicates an oligonucleotide with a molecular weight, which is greater than or equal to 1 bp and lower than 100 bp (less than 5 monomers). Oligonucleotide includes siRNA, DNA, RNA and antisense nucleotide, which are used for biological researches and medical disease treatment.

Also, "high-molecular oligonucleotide" indicates an oligonucleotide with a high molecular weight, and in the present disclosure may have a molecular weight, which is greater than or equal to 100 bp and lower than 40000 bp (5 to 2000 monomers).

The high-molecular oligonucleotide may be prepared by physically or chemically binding oligonucleotides with small molecular weights. The physical bond may be selected from hydrogen bonds, potential bonds, charge couplings, van der Waals bonds, hydrophobic bonds and hydrophilic bonds, and the chemical bond may be selected from disulfide bonds, diamine bonds, sulfide-amine bonds, carboxyl-amine bonds, ester bonds and covalent bonds. Those physical bond and chemical bond may allow the oligonucleotides with a small molecular weight to be prepared into high-molecular oligonucleotides with various molecular weights. The high-molecular oligonucleotide may preferably be prepared by the chemical bond. Polymerization of oligonucleotides with small molecular weights by the chemical bond such as the disulfide bond may allow preparation of high-molecular siR-NAs with various molecular weights, as compared to polymerization by the physical bond, and also ensure an increased anionic property and structural stability, so a more increased in vivo stability can be obtained.

As one example, the oligonucleotide may preferably be siRNA, especially, siRNA consisting of 15 to 30 nucleotides. The siRNA may inhibit expression of a specific gene in a living body, so it may be useful for a gene therapy. Meanwhile, in order to improve in vivo stability, the low-molecular siRNA oligonucleotide may be prepared into a high-molecular oligonucleotide. Low-molecular siRNAs whose both terminals are thiol groups (—SH groups) may be bonded via chemical crosslinikings through a disulfide bond, thus to prepare a high-molecular siRNA oligonucleotide (see FIG. 1).

Also, "high-molecular oligonucleotide carrier system" indicates a material for delivering a high-molecular oligonucleotide into a living body, and is prepared by binding a high-molecular oligonucleotide, which is prepared by polymerizing oligonucleotides, such as low-molecular siRNAs, DNAs, RNAs, antisense nucleotides and the like, to hydrophilic high-molecular materials or inorganic materials. Since the high-molecular oligonucleotide prepared in this specification has a plurality of negative (−) charges, it may be bound to hydrophilic high molecules with positive potentials or inorganic materials. The oligonucleotide, especially, siRNA exhibits a low negative potential due to its low molecular weight, unlike a high-molecular oligonucleotide (DNA) used as a drug for a gene therapy, and accordingly binds even to a high-molecular material with a positive potential by a relatively weak bond, which may cause degradation and a side effect during a cell absorption process and in a living body. Therefore, upon binding the hydrophilic high-molecular materials with the positive potential into nanoparticle composites, it may be favorable in view of enhancing in vivo stability much more. Alternatively, upon binding biocompatible inorganic materials, such as iron oxide, gold and the like, it may be useful because such materials may have a further increased molecular weight to be retentive in a living body for a long term.

Any hydrophilic high-molecular material with biocompatibility may be used, without limitation, as the hydrophilic high-molecular material capable of binding to the siRNA oligonucleotide. Especially, a high-molecular material with high disease tissue retention efficiency may be used. Such hydrophilic high-molecular material should have high biocompatibility and biodegradation to obtain high in vivo stability and high bio concentration in blood, such that the material can be continuously accumulated on disease cells or tissues such as cancer tissues for a sufficient time. Possible examples of such hydrophilic high-molecular materials may include bio high-molecular materials, such as dextran, chitosan, glycol chitosan, poly-L-lysine, poly-aspartic acid and the like, and synthetic high-molecular materials, such as polyethylene imine (PEI), poly(N-2-(hydroxypropyl)methacrylamide), poly(divinyl ether-co-maleic anhydroide), poly(styrene-co-maleic anhydride), poly(ethylene glycol) and the like.

Among those high-molecular materials, the polyethyleneimine (PEI, Mw 25K, 1.8K) contains plentiful positrons at high-molecular chains, so it may be appropriate to bind to oligonucleotide such as siRNA or the like. The polyethyleneimine used in the present disclosure may have a molecular weight in the range of $10^2$ to $10^5$ bp on the average.

The oligonucleotide such as siRNA and the high-molecular material such as polyethylene imine (PEI) may bind to each other by a physical bond or a chemical bond. Among others, a potential bond may be favorable to physically bind them. The method may support maximum 95% of intake quantity, which is far higher than the maximum intake quantity of the chemical bond, which is limited to about 10%. Thus, the physical bond can overcome the limitation upon the chemical bond, thereby remarkably increasing a drug content.

Figure 4:
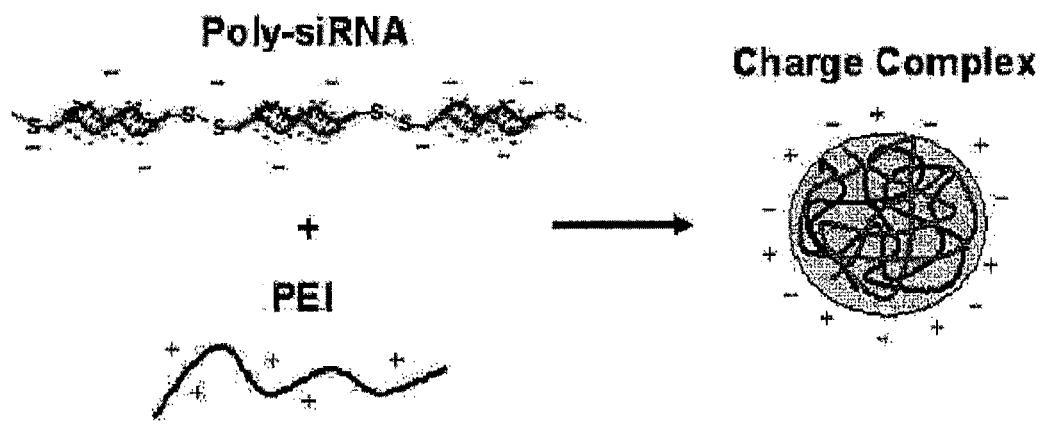
FIG. 4 shows a method for preparing a high-molecular oligonucleotide carrier system (nanoparticle) using a polymerized high-molecular oligonucleotide (poly-siRNA) and polyethyleneimine (PEI) (Mw 25K, 1.8K) with positive charges.

As such, the composite prepared by binding the high-molecular oligonucleotide such as siRNA and the hydrophilic high-molecular materials can exhibit high in vivo stability and suppress expression of a specific gene of various diseases (e.g., cancer) or disease cells, so it can be effectively used for disease (e.g., cancer) prevention and/or disease therapy. The composite may be a type of amphiphilic nanoparticle and be within 10 to 2000 nm in size (see FIG. 4), preferably, in 10 to 800 nm.

Any type of siRNA may be used in the present disclosure, for example, a type of siRNA, which is helpful to treat diseases, such as the lungs (RSV, Flu, SARS, influenza), eyes (AMD), a nerve system (depression, Alzheimer, Huntington disease, Spincoerebral ataxia, ALS, neuropathic pain, Encephalitis), cancers (glioblastoma, human paillomavirus, prostate, adenocarcinoma), a digestive system (irritable bowel disease, the liver (HBV, hypercholesterolemia), joints (rheumatoid arthritis), a genital system (HSV) and the like.

The high-molecular oligonucleotide, namely, siRNA may be contained in a carrier system by 99% by weight with respect to the total weight.

In the meantime, the high-molecular oligonucleotide prepared by the polymerization method may be used as a significant component of a pharmacological composition for treatment of a specific disease. Therefore, this specification provides a pharmacological composition consisting of an effective dose (amount) of oligonucleotide with a high-molecular weight.

The pharmacological composition may further consist of one or more types of pharmacologically allowable carriers in addition to the oligonucleotide carrier system.

The pharmacological allowable carriers may be compatible with the significant component. As the pharmacological allowable carrier, saline solution, sterile water, ringer's solution, buffered saline water, dextrose solution, maltodextrin solution, glycerol, ethanol and a mixture of at least one thereof may be used, or if necessary, other typical excipient, such as antioxidant, buffer solution, bacteriostatic agent and the like, may be added. Also, diluent, dispersing agent, surfactant, binder and lubricant may additionally be added to be prepared into a formation for injection, such as aqueous solution, suspension, emulsion and the like.

The pharmacological composition may be prepared into various forms, such as powders, tablet, capsule, liquid medicine, injection, ointment, syrup and the like, and be provided by use of a unit-dosage or multi-dosage container, for example, a sealed ampule and bottle and the like.

The pharmacological composition may be allowed for oral or parenteral administration. Administrations of the pharmacological composition may be carried out by one of methods including, but not limited to, oral administration, intravenous administration, intramuscular administration, intraarterial administration, intramedulary administration, intramural administration, intracardiac administration, transcutaneous administration, subcutaneous administration, intraperitoneal administration, intestinal administration, sublingual administration or local administration. The pharmacological composition may be prepared into an appropriate formation by using well-known technologies for such clinical administrations. For example, upon an oral administration, the pharmacological composition may be mixed with an inactive diluent or edible carrier, sealed in a hard or soft gelatin capsule or pressed into tablets for administration. For the oral administration, the active compound may be mixed with a diluting agent to be used in form of ingestible tablet, buccal tablet, troche, capsule, elixirs, suspension, syrup, wafer and the like. Also, various formations for, for example, injection, parenteral administration and the like may be fabricated according to known techniques in the field of this specification or a commonly used technique.

The dosage of the composition may vary within a wide range according to weight, age, gender, health status, diet, administration time, administration manner, excretion rate, severity of disease and the like, all related to patients, and be decided by typical exports in the art the present disclosure belongs to.

Hereinafter, description will be given in detail of the exemplary embodiments.

Here, the following embodiments are merely illustrative, and should not be construed to limit the present disclosure.

Example 1

Preparation of High-Molecular Oligonucleotide (Poly-siRNA (RFP))

2 mg of dithiol-siRNA (RFP) was melted in 10 µl of 10 mM HEPES buffer (1 mM EDTA, pH 8.0) to be stirred at room temperature for 12 hours, thereby preparing various high-molecular oligonucleotides (poly-siRNA (RFP)), which had a disulfide bond and a molecular weight in the range of 160 to 2000 bp (see FIG. 1).

Example 2

Figure 2:
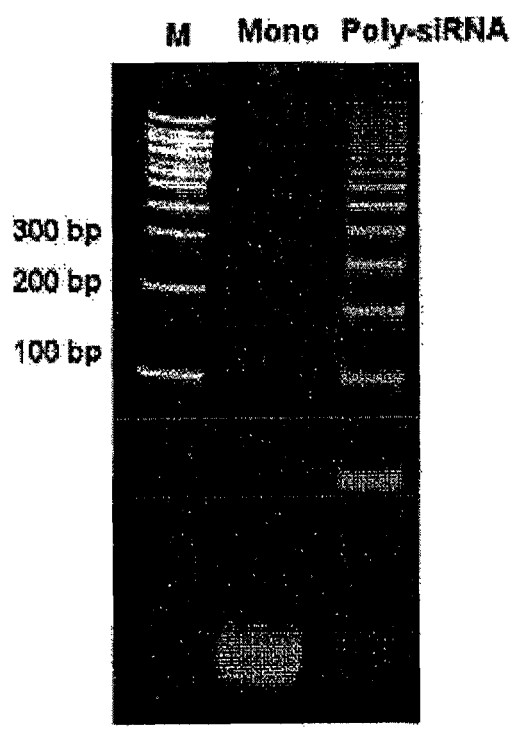
FIG. 2 shows electrophoresis test results of the changes in a molecular weight before and after the oligonucleotide (siRNA) having -thiol group (—SH group) at both terminals is chemically polymerized in Example 1.

Molecular Weight Comparison of Oligonucleotide (Mono-siRNA (RFP)) and High-Molecular Oligonucleotide (Poly-siRNA (RFP)) Through Electrophoresis 500 ng/1 µl of oligonucleotides (mono-siRNA (RFP)) with a molecular weight of 21 bp and high-molecular weight oligonucleotides (poly-siRNA (RFP)), both which were dissolved in the HEPES buffer (pH 8.0), were mixed with 1 µl of loading buffer and 8 µl of DEPC water. Such mixture was loaded in 8% acrylamide gel together with a molecular weight marker (100 bp ladder), followed by an electrophoresis under condition of 150V for 35 minutes. Afterwards, SyBr-gold staining was performed to confirm a polymerized pattern via a fluorescent image. It was exhibited through the comparison with the marker that various high-molecular oligonucleotides (poly-siRNA (RFP)) with molecular weights in the range of 160 to 2000 bp were prepared (see FIG. 2).

Example 3

Figure 3:
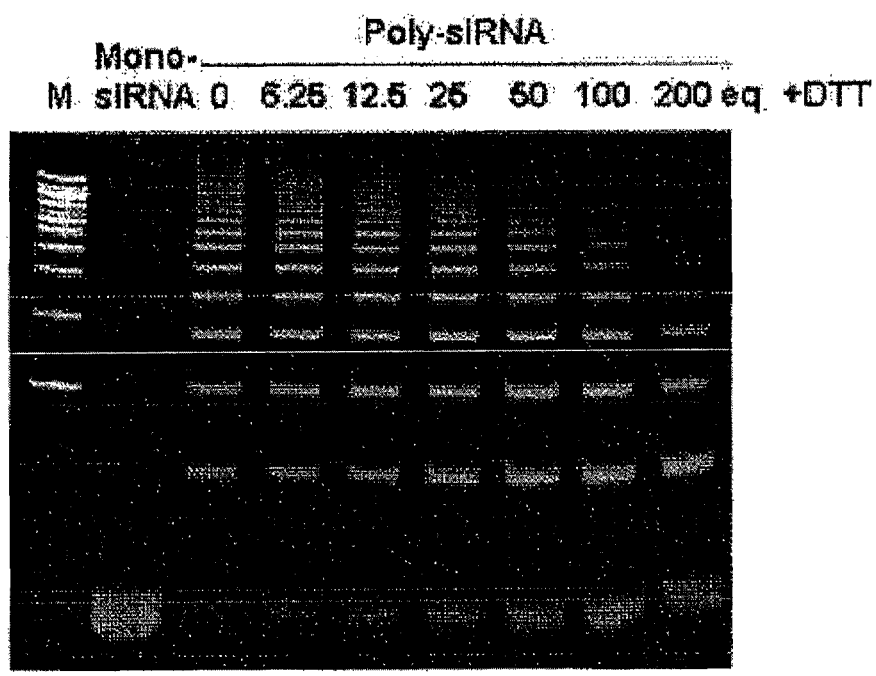
FIG. 3 shows electrophoresis test results of the oligonucleotides (siRNA) polymerized in Example 1 being depolymerized by Dithiothreitol (DTT) according to concentration.

Confirmation of Depolymerization of High-Molecular Oligonucleotide (Poly-siRNA (RFP)) According to Dithiothreitol (DTT) Concentration Through Electrophoresis 10 µg/10 µl of high-molecular oligonucleotides (poly-siRNA (RFP)) melted in the HEPES buffer (pH 8.0) were mixed with 200-1 times mol excess of DTT (25 µg/10 µl-0 µg/10 µl), respectively. The mixture was left as it was at 37° C. for 90 minutes, followed by the electrophoresis the same as that in Example 2, thereby obtaining a fluorescent image. As shown in FIG. 3, it was confirmed that the high-molecular oligonucleotides were degraded into oligonucleotides (mono-siRNA (RFP)) by the DTT, which lysed a disulfide bond (see FIG. 3). That is, it was exhibited that the bonding of the high-molecular oligonucleotides was enabled by the disulfide bond.

Example 4

Preparation of High-Molecular Oligonucleotide (Poly-siRNA (RFP))/PEI (Mw 25K, 1.8K) Nanoparticle 20 µg/10 µl of oligonucleotides (mono-siRNA (RFP)) with a molecular weight of 21 bp and high-molecular oligonucleotides (poly-siRNA (RFP)) with a molecular weight in the range of 160~2000 bp, both were dissolved in the HEPES buffer (pH 8.0), were mixed with 25K polyethyleneimine in an excessive weight of 200 µg/10 µl, respectively, followed by mixing with 1.8K polyethyleneimine in weight excess of 0 µg/10 µl (cases of 10 to 0 time; 0 time were used as control groups). The mixture was left as it was at room temperature for 30 minutes. The schematic diagram was shown in FIG. 4.

Example 5

Figure 5:
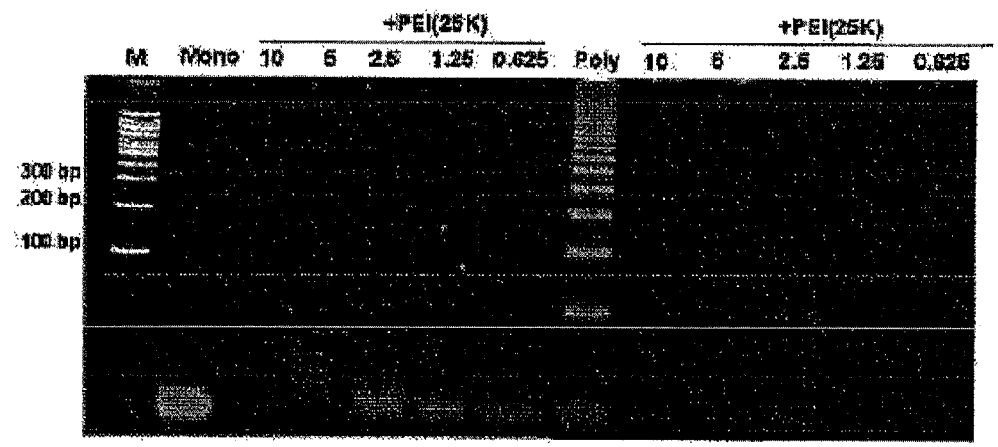
FIG. 5 shows a fluorescent image obtained by performing an electrophoresis with respect to nanoparticles, prepared by binding the polymerized oligonucleotide (poly-siRNA) to polyethyleneimine (PEI) (25K), and oligonucleotides.

Stability Test for High-Molecular Oligonucleotide (Poly-siRNA (RFP))/PEI (Mw 25K) Nanoparticle The oligonucleotide (mono-siRNA (RFP) or high-molecular oligonucleotide (Poly-siRNA (RFP))/PEI (Mw 25K)

nanoparticles prepared in Example 4 were electrophoresed the same as done in Example 2, thereby obtaining a fluorescent image. It was exhibited that the high-molecular oligonucleotides (poly-siRNA (RFP)) were mixed with PEI (25K) in weight excess of 5 times to prepare a composite more stable than the oligonucleotide (mono-siRNA (RFP)). (see FIG. 5).

Example 6

Figure 6:
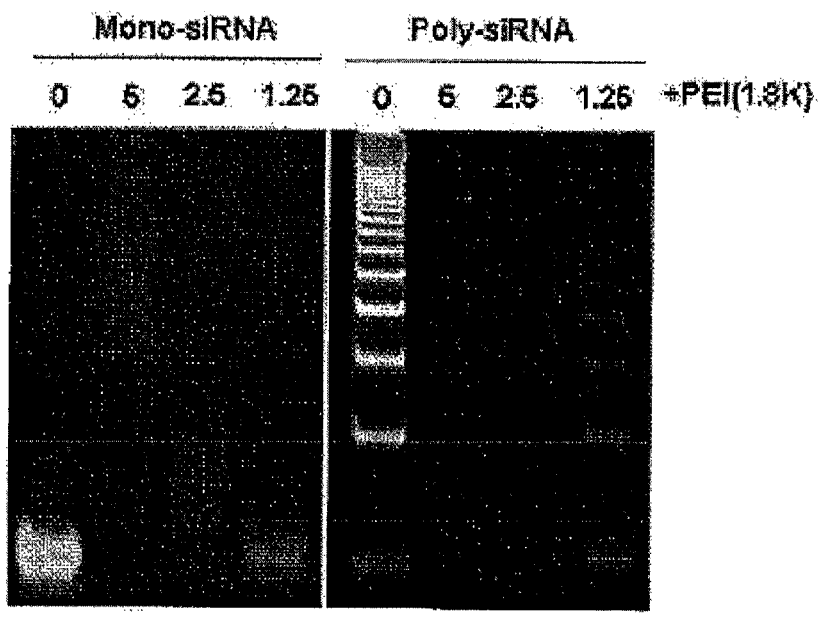
FIG. 6 shows a fluorescent image obtained by performing an electrophoresis with respect to nanoparticles, prepared by binding the polymerized oligonucleotide (poly-siRNA) to polyethyleneimine (PEI) (1.8K), and oligonucleotides.

Stability Test for High-Molecular Oligonucleotide (Poly-siRNA (RFP))/PEI (Mw 1.8K) Nanoparticle The oligonucleotide (mono-siRNA (RFP) or high-molecular weight oligonucleotides (Poly-siRNA (RFP))/PEI (Mw 1.8K) nanoparticles prepared in Example 4 were electrophoresed the same as done in Example 2, thereby obtaining a fluorescent image (see FIG. 6). It was exhibited that the high-molecular oligonucleotides (poly-siRNA (RFP)) were mixed with PEI (1.8K) in weight excess of 2.5 times to prepare a composite more stable than the oligonucleotide (mono-siRNA (RFP)). (see FIG. 6).

Example 7

Effect Estimation of High-Molecular Oligonucleotide (Poly-siRNA (RFP))/PEI (Mw 25K) Nanoparticle as Oligonucleotide (siRNA) Carrier System Through Cell Experiment The oligonucleotide (mono-siRNA (RFP) or high-molecular oligonucleotide (Poly-siRNA (RFP))/PEI (Mw 25K) (weight ratio of 5:1) nanoparticles prepared in Example 4 and Example 5 were mixed with REP-B16/F10 ($1.2*10^5$/dish) cells, in which RFP was expressed, together with control groups (control, mono-siRNA (RFP)) and poly-siRNA (RFP)), in oligonucleotide concentrations of 50 nM and 25 nM, respectively, and images exhibiting RFP expression inhibition efficacy were acquired after 24 hours.

Figure 7:
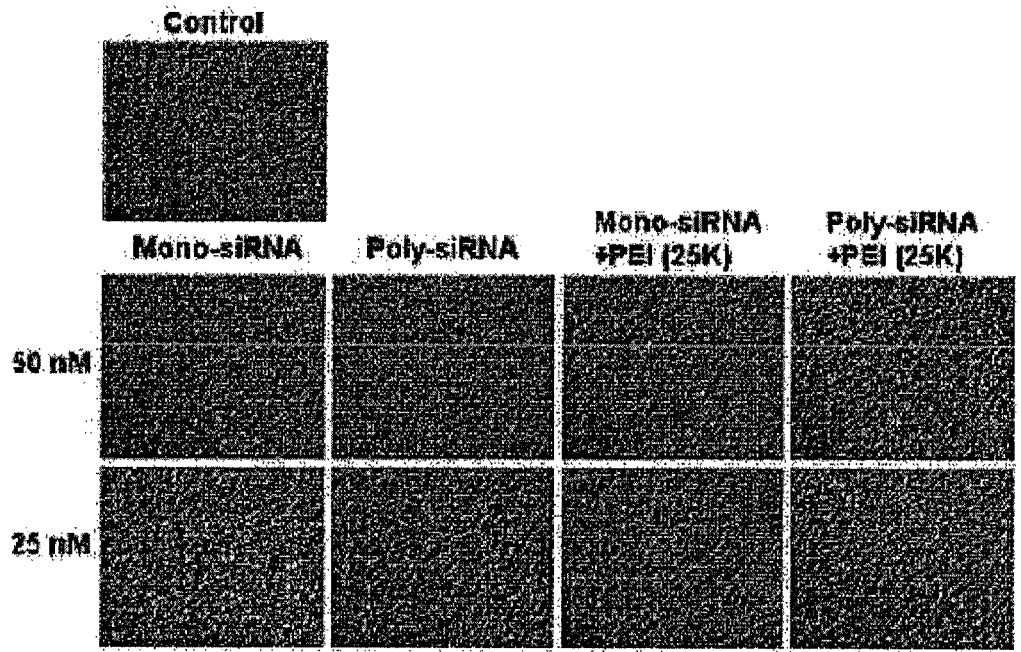
FIG. 7 shows an in vivo test according to concentrations of oligonucleotide (poly-siRNA (RFP))/PEI (Mw 25K) nanoparticles prepared in Example 5.

FIG. 7 shows results of comparing images, which show that the high-molecular oligonucleotides (Poly-siRNA (RFP))/PEI (Mw 25K) nanoparticles are used to transfer the oligonucleotides (siRNA (RFP)) into cells and perform an action (RFP expression inhibition), with the control groups. As shown in FIG. 7, the high-molecular oligonucleotide nanoparticle exhibited higher in vivo concentration.

Example 8

Effect Estimation of High-Molecular Oligonucleotide (Poly-siRNA (RFP))/PEI (Mw 1.8K) Nanoparticle as Oligonucleotide (siRNA) Carrier System Through Cell Experiment The oligonucleotides (mono-siRNA (RFP) or high-molecular oligonucleotides (Poly-siRNA (RFP))/PEI (Mw 1.8K) (weight ratio of 2.5:1) nanoparticles prepared in Example 4 and Example 5 were mixed with RFP-B16/F10 ($1.2*10^5$/dish) cells, in which RFP was expressed, together with control groups (control, mono-siRNA (RFP)) and poly-siRNA (RFP)), in oligonucleotide (siRNA (RFP)) concentrations of 400 nM, 200 nM and 100 mM, respectively, and images exhibiting RFP expression inhibition efficacy were acquired after 24 hours.

Figure 8:
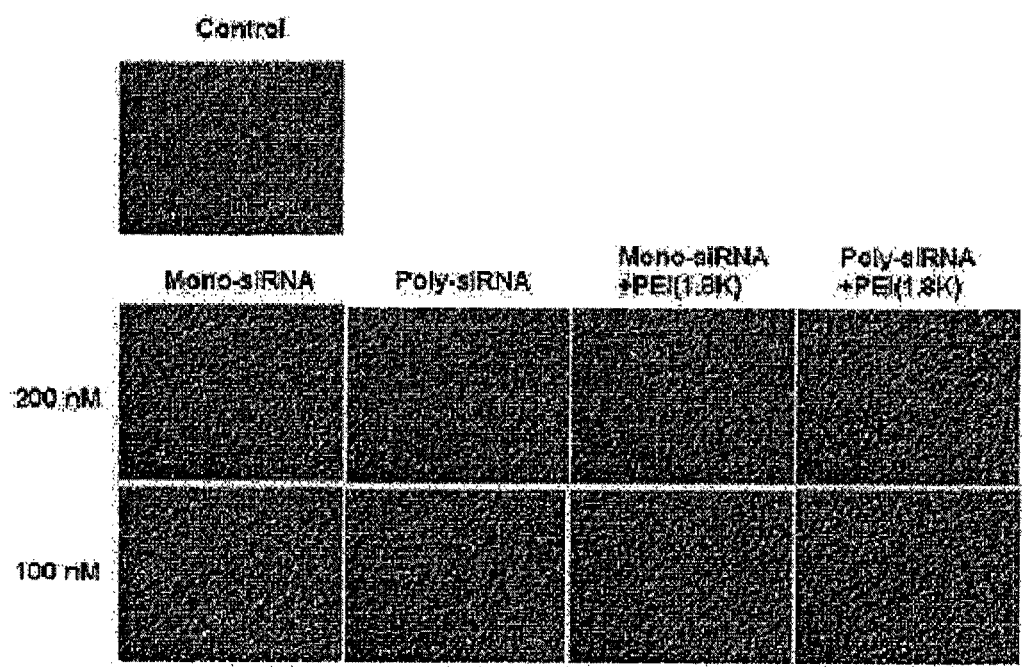
FIG. 8 shows an in vivo test according to concentrations of oligonucleotide (poly-siRNA (RFP))/PEI (Mw 1.8K) nanoparticles prepared in Example 5.

FIG. 8 shows a result a result of comparing images, which show that the high-molecular oligonucleotide (Poly-siRNA (RFP))/PEI (Mw 1.8K) nanoparticles are used to transfer oligonucleotides (siRNA (RFP)) into cells and perform an action (RFP expression inhibition) therein, with the control groups.

The invention claimed is:

1. A polymer of oligonucleotides (poly-oligonucleotide) having a molecular weight of about 100 to about 40000 base pairs, comprising about 5 to about 2000 mono-oligonucleotides connected with each other by physical or chemical bonds,
    wherein the mono-oligonucleotide has a molecular weight of about 1 to about 100 base pairs, and the poly-oligonucleotide has an enhanced in vivo stability compared with the mono-oligonucleotide.

2. The poly-oligonucleotide of claim 1, wherein the oligonucleotide is selected from the group consisting of DNA, RNA, siRNA and antisense oligonucleotide.

3. The poly-oligonucleotide of claim 1, wherein the mono-oligonucleotide is siRNA consisting of 15 to 30 base pairs.

4. The poly-oligonucleotide of claim 3, wherein the siRNA treats a disease selected from the group consisting of lung diseases such as RSV, Flu, SARS, and influenza; eye diseases such as AMD; diseases in nervous system such as depression, Alzheimer, Huntington disease, Spincoerebral ataxia, ALS, neuropathic pain, and Encephalitis; cancers such as glioblastoma, human papillomavirus-induced cancer, prostate cancer, and adenocarcinoma; diseases in digestive system such as irritable bowel disease; liver diseases such as HBV and hypercholesterolemia; diseases in joints such as rheumatoid arthritis; and diseases in genital system such as HSV.

5. The poly-oligonucleotide of claim 1, wherein the physical bond is selected from hydrogen bond, potential bond, charge coupling, Van der Waals bond, hydrophobic bond and hydrophilic bond.

6. The poly-oligonucleotide of claim 1 wherein the chemical bond is selected from disulfide bonds, diamine bonds, sulfide-amine bonds, carboxyl-amine bonds, ester bonds and covalent bonds.

7. A poly-oligonucleotide carrier system comprising:
    (i) the poly-oligonucleotide of claim 1; and
    (ii) a synthetic polymer or a biocompatible inorganic material, connected with the poly-oligonucleotide,
    wherein the synthetic polymer is selected from the group consisting of polyethyleneimine (PEI), poly(N-2-(hydroxypropyl)methacrylamide), poly(divinyl ether-co-maleic anhydroide), poly(styrene-co-maleic anhydride) and poly(ethylene glycol), and
    wherein the biocompatible inorganic material is selected from iron oxide and gold.

8. The poly-oligonucleotide carrier system of claim 7, wherein the poly-oligonucleotide carrier system is a type of amphiphilic nanoparticle.

9. The poly-oligonucleotide carrier system of claim 8, wherein the amphiphilic nanoparticle has a diameter of about 10 to about 800 nm.

10. The poly-oligonucleotide carrier system of claim 8, wherein the amphiphilic nanoparticle has a diameter of about 10 to about 2000 nm.

11. The poly-oligonucleotide carrier system of claim 8, wherein the poly-oligonucleotide carrier system comprises about 1 to about 99% by weight of the poly-oligonucleotide.

12. The poly-oligonucleotide carrier system of claim 8, wherein the poly-oligonucleotide carrier system forms spherical self-aggregates in water system.

* * * * *